(12) United States Patent
McLean et al.

(10) Patent No.: US 10,932,989 B1
(45) Date of Patent: Mar. 2, 2021

(54) MEDICAL TRANSPORT CONTAINER FOR PHARMACEUTICALS

(71) Applicant: Mark-Anthony McLean, Plantation, FL (US)

(72) Inventors: Mark-Anthony McLean, Freeport, NY (US); Audrey Angela McLean, Freeport, NY (US)

( * ) Notice: Subject to any disclaimer, the term of this patent is extended or adjusted under 35 U.S.C. 154(b) by 120 days.

(21) Appl. No.: 16/037,390

(22) Filed: Jul. 17, 2018

Related U.S. Application Data

(60) Provisional application No. 62/534,560, filed on Jul. 19, 2017.

(51) Int. Cl.
| | |
|---|---|
| *F25B 11/00* | (2006.01) |
| *A61J 1/12* | (2006.01) |
| *F25D 3/06* | (2006.01) |
| *F25D 3/08* | (2006.01) |
| *A61J 1/16* | (2006.01) |
| *B65D 81/38* | (2006.01) |
| *A61B 50/10* | (2016.01) |
| *A61B 50/00* | (2016.01) |

(52) U.S. Cl.
CPC .............. *A61J 1/165* (2013.01); *A61B 50/10* (2016.02); *B65D 81/38* (2013.01); *A61B 2050/0014* (2016.02)

(58) Field of Classification Search
CPC ...... F25D 11/00; F25D 11/003; F25D 11/006; F25D 2303/083; F25D 2303/0831; F25D 2303/0832; F25D 2303/0843; F25D 2303/0846; F25D 3/06; F25D 3/08; A61J 1/12; A61J 1/165

See application file for complete search history.

(56) References Cited

U.S. PATENT DOCUMENTS

| | | | | |
|---|---|---|---|---|
| 3,802,220 | A * | 4/1974 | Pompo | F25D 3/00 |
| | | | | 62/530 |
| 4,367,633 | A * | 1/1983 | Strathman | F25B 27/002 |
| | | | | 62/236 |
| 6,073,789 | A * | 6/2000 | Lundblade | B65D 81/3825 |
| | | | | 220/4.22 |
| 7,040,115 | B1 * | 5/2006 | Lopez | F25D 3/08 |
| | | | | 62/371 |

(Continued)

*Primary Examiner* — Frantz F Jules
*Assistant Examiner* — Erik Mendoza-Wilkenfel

(57) ABSTRACT

The present invention is directed to a medical device, specifically, a medical transport container for transporting blood and/or pharmaceuticals, e.g. human or animal medication, which are temperature sensitive, and comprises a forming gel encapsulated within the main storage compartment, which may comprise of one or more removable dividers to accommodate a plurality of blood vials or pharmaceuticals being cooled by a refrigerating element and/or the forming gel, which morphs and conforms to hold the container's inner contents (i.e. pharmaceutical(s), blood, test tube and/or vial(s) and the like) firmly in place. Accordingly, the content(s) may be transported over long distances in a sterile climate-controlled environment, where the temperature can be preset and consistently maintained for much longer duration using a plurality of power sources, e.g. battery pack with one or more rechargeable batteries supplying power for the trip's duration, in essence preserving the transported content's lifespan and viability.

9 Claims, 4 Drawing Sheets

(56) References Cited

U.S. PATENT DOCUMENTS

| | | | | |
|---|---|---|---|---|
| 2007/0028642 A1* | 2/2007 | Glade | ............. | A45C 11/20 |
| | | | | 62/371 |
| 2012/0019356 A1* | 1/2012 | Gagneraud | ............. | G06F 21/32 |
| | | | | 340/5.32 |
| 2013/0193673 A1* | 8/2013 | Vanderberg | ............. | B62B 3/16 |
| | | | | 280/655 |
| 2015/0369529 A1* | 12/2015 | Monroe | ............. | F25D 3/08 |
| | | | | 62/457.2 |
| 2016/0153690 A1* | 6/2016 | Patsis | ............. | F25D 3/08 |
| | | | | 222/608 |

* cited by examiner

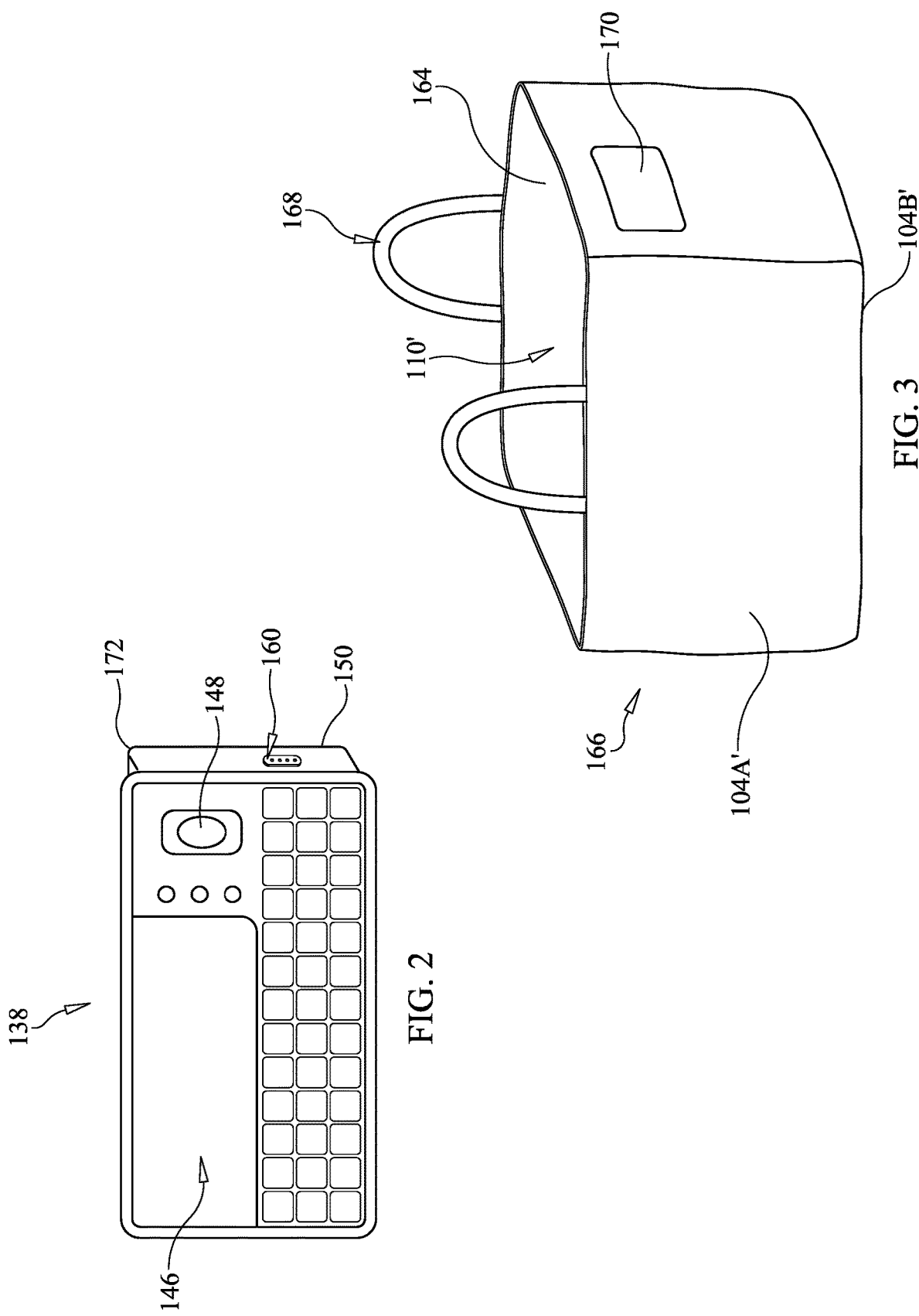

MEDICAL TRANSPORT CONTAINER FOR PHARMACEUTICALS

PRIORITY CLAIM

This patent application is a Non-Provisional patent application and claims priority under 35 U.S.C. § 119(e) to U.S. Provisional Patent Application Ser. No. 62/534,560, titled "A Medical Transport Container" filed Jul. 19, 2017. The entire disclosure of the aforementioned patent application is incorporated by reference as if fully stated herein.

FIELD OF THE INVENTION

The present invention is directed to a medical device, specifically, a medical transport container for transporting blood and/or pharmaceuticals, e.g. human or animal medication, which are temperature sensitive. Medical transport container comprises a forming gel encapsulated within the main storage compartment, which may comprise of one or more removable dividers to accommodate a plurality of blood vials or pharmaceuticals being cooled by a refrigerating element and/or the forming gel, which morphs and conforms to hold the container's inner contents (i.e. pharmaceutical(s), blood, test tube and/or vial(s) and the like) firmly in place. Accordingly, the content(s) may be transported over long distances in a sterile climate-controlled environment, where the temperature can be preset and consistently maintained for much longer duration using a plurality of power sources, e.g. battery pack with one or more rechargeable batteries supplying power for the trip's duration, in essence preserving the transported content's lifespan and viability.

BACKGROUND OF THE INVENTION

Both blood and certain pharmaceuticals e.g. refrigerated biologics, can be temperature sensitive requiring a rigorous process, e.g. where the U.S. Food and Drug Administration mandates that they are stored and transported within 2° C. to 8° C. (36° F. to 46° F.), unless the pharmaceuticals are deemed stable at other temperature ranges. Thus, in order for the blood and/or pharmaceutical to remain viable, it is of utmost importance that the transportation logistics are well planned well with careful and meticulous arrangements from procurement to delivery, e.g. blood and/or pharmaceutical(s) may be secured in a sealed cooler and transported by land or air, to a facility where the patient is located, maintaining the prescribed optimum temperature during the transportation process to ensure the integrity and viability of the pharmaceutical upon delivery.

The current state of the art includes use of various storage containers, from the very simple to complex containers, which may include one or more compartments for storing and maintaining for example, the pharmaceutical during transport, and including ice for maintaining the desired temperature. In order to accommodate the significant amount of ice needed, the prefabricated compartments often limit the flexibility and quantity of blood or pharmaceutical(s) that can be transported. Additionally, over a prolonged period of time ice melts into water, which may compromise the integrity of the content.

Alternatively, dry ice may be used because of its temperature and its ability to keep items cold for prolonged periods of time, since dry ice simply evaporates without leaving a water residue at the bottom of the container, and more importantly, keeping the pharmaceutical clear of water. However, neither solution fully resolves the issues if there are unforeseen delays during transportation or delivery, as the content is either subject to a watery environment, or if dry ice is used, once the dry ice evaporates, there is nothing remaining to keep the blood or pharmaceutical cool, much less at the desired temperature.

Other current alternatives may include a container, e.g. an ice chest, with frozen gel packs or chemical ice packs as the cooling agent. However, chemical packs are not always reliable and the frozen gel packs lack sustainability for prolonged hours. Therefore, there is a long-standing need for an apparatus/container for blood and/or pharmaceutical transport that allows a high degree of viability with little or no variation in temperature during transport over a prolonged period of time. This invention satisfies these long felt needs and solves the limitations of the prior art in a new and novel manner.

For a further and more fully detailed understanding of the present invention, various objects and advantages thereof, reference is made to the following detailed description and the accompanying drawings.

The foregoing and other objects and advantages will appear from the description to follow. In the description, references are made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views. The following detailed description is, therefore, not to be taken in a limiting sense, and the scope of the present invention is best defined by the appended claims.

SUMMARY OF THE INVENTION

The present disclosure results from the realization that blood and/or pharmaceuticals may be conveniently transported over long distances for a prolonged period of time in a sterile environment at a consistent desired temperature, which aids in fighting off bacteria, creating a sterile environment, which is optimum for the viability and efficacy for delivery to the patient.

An aspect of an embodiment of the present invention contemplates an exemplary apparatus according to an embodiment of the present invention comprising an outer casing comprising of at least two rigid walls, an outer perimeter wall and a bottom wall, wherein the outer perimeter wall extends upward and substantially around the outer perimeter of the outer casing, abutting and cooperating with the bottom wall that is disposed perpendicularly to the outer perimeter wall, together forming an inner cavity adapted to form an inner receptacle area; the inner cavity includes a liner formed from an impermeable material, substantially engaging the inner cavity, lining the inner walls of the inner cavity and abutting the container's top, and including a flexible forming gel encapsulated/disposed between the inner cavity and the liner, wherein the forming gel morphs and conforms to a shape of the content within the inner receptacle area, holding the content secure and firmly in place; an openable lid hingedly attached to the top of the container and the inner receptacle area; and a refrigerating element capable of maintaining temperature within a prescribed temperature range for extended periods of time upon being activated.

An aspect of an embodiment of the present invention contemplates the lid further comprising insulation and/or the liner, which includes the forming gel, providing overhead support from the lid for the container's contents.

An aspect of an embodiment of the present invention contemplates a monitoring unit securely mounted on the apparatus' outer casing, wherein the monitoring unit further comprising authentication means that may be any one or more of the following: password verification, keys, and/or biometric verification means. Such biometric verification means may comprise of a biometric verification module that includes hardware and software aspects, e.g. a computer processor disposed in communication with a biometric scanner, and/or a user interface, where the biometric scanner may be any of any one or more of the following: a fingerprint scanner, facial scanner, hand geometry scanner, a palm geometry scanner, iris scanner, and/or retina scanner.

An aspect of an embodiment of the present invention further contemplates a base comprising of a housing shaped to substantially enclose the bottom of the apparatus within the housing's primary aperture, where the housing is adapted to be releasably locked together with the main storage compartment in a connected position forming a unitary device with the medical transport container, such that the apparatus would not otherwise require a bottom panel cover for the apparatus' internal battery(ies) positioned within.

An aspect of an embodiment of the present invention contemplates a power source that may include any one or more of the following: a rechargeable battery, an AC charger, and/or a charger port operably engaged with the monitoring unit providing a source of power for its operability. Monitoring unit may also comprise of communication means that may include a wireless transmitter or a transceiver.

An aspect of an embodiment of the present invention contemplates a pouch that comprises of at least two or more walls cooperating together, connecting and defining an open receptacle area that accommodates the apparatus. The pouch may comprise of insulation and carrying means that includes but is not limited to any one or more of the following: adjustable shoulder strap, handle, or handgrip. Pouch also comprises of a viewing window defined by an aperture within the pouch's perimeter wall, wherein the viewing window may include a transparent film adhered to, and covering the aperture thereby defining the viewing window.

BRIEF DESCRIPTION OF THE DRAWINGS

Further objectives and advantages of the present invention may be derived by referring to the detailed description and claims when considered in connection with the Figures. The present invention is illustrated by way of example and not limitation in the accompanying figures, wherein like reference numbers refer to similar items throughout the Figures.

FIG. 2 shows the monitoring unit of the apparatus in accordance with one embodiment.

FIG. 3 shows the pouch of the apparatus in accordance with one embodiment.

DETAILED DESCRIPTION OF PREFERRED EMBODIMENTS

Figure 1A:
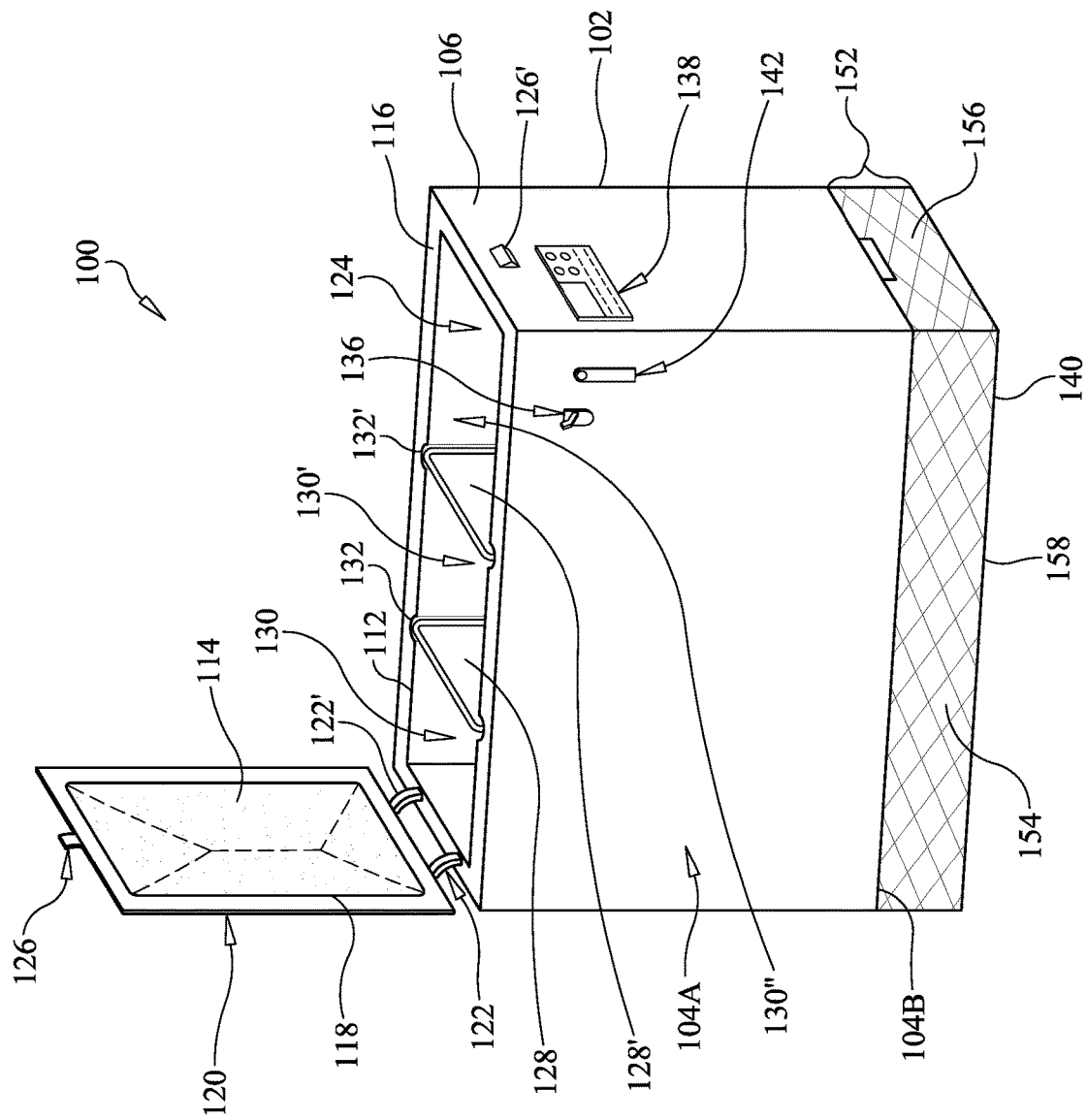
FIG. 1A shows an apparatus in accordance with one embodiment.

The following discussion describes in detail, an embodiment of the apparatus, as described below. However, this discussion should not be construed, as limiting the invention to those particular embodiments, as practitioners skilled in the art will appreciate that an apparatus may vary as to configuration and as to details of the parts, without departing from the basic concepts as disclosed herein. Similarly, the elements described herein may be implemented separately, or in various combinations without departing from the teachings of the present invention. Turning now descriptively to the drawings, in which similar reference characters denote similar elements throughout the several views.

Figure 1B:
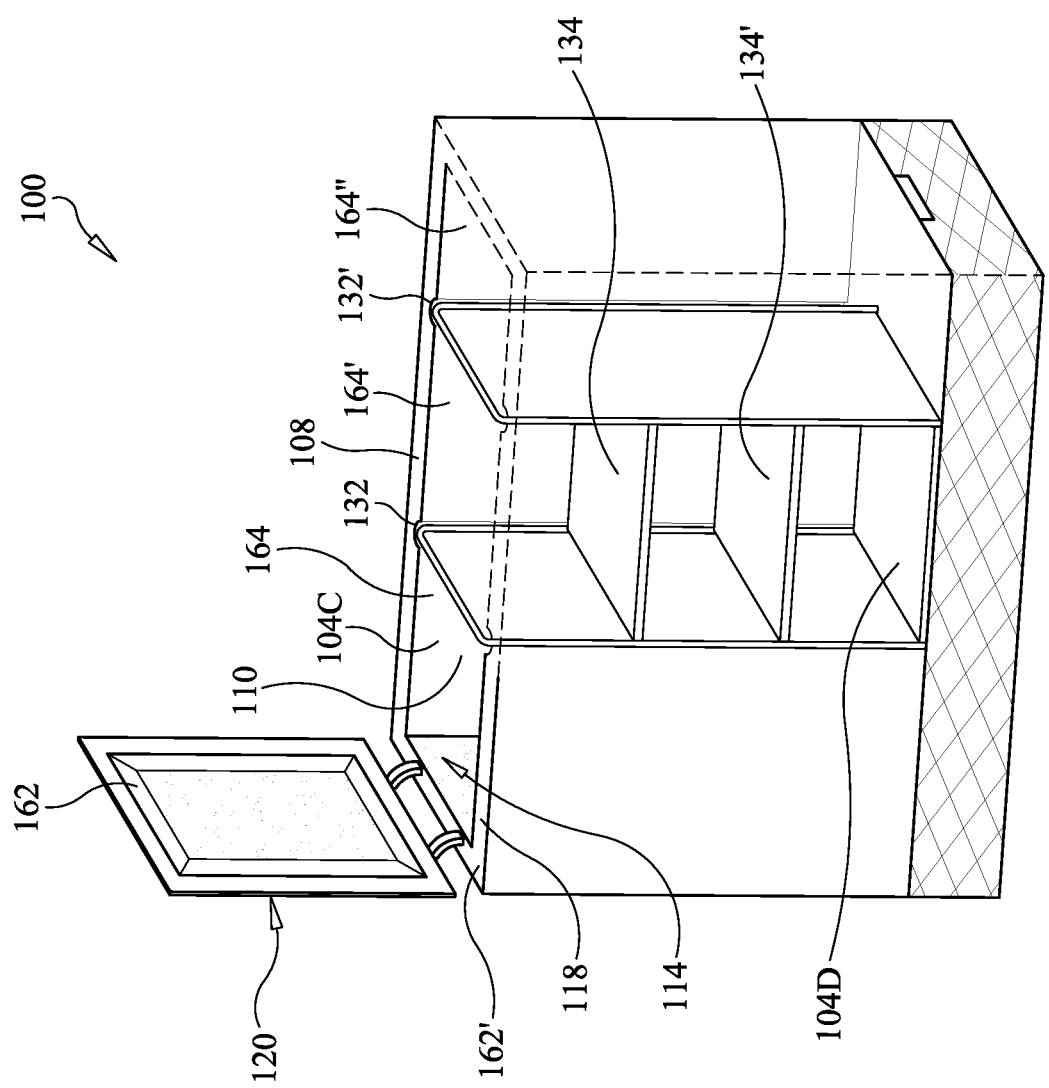
FIG. 1B shows a cross section of the apparatus in accordance with one embodiment.
Figure 1C:
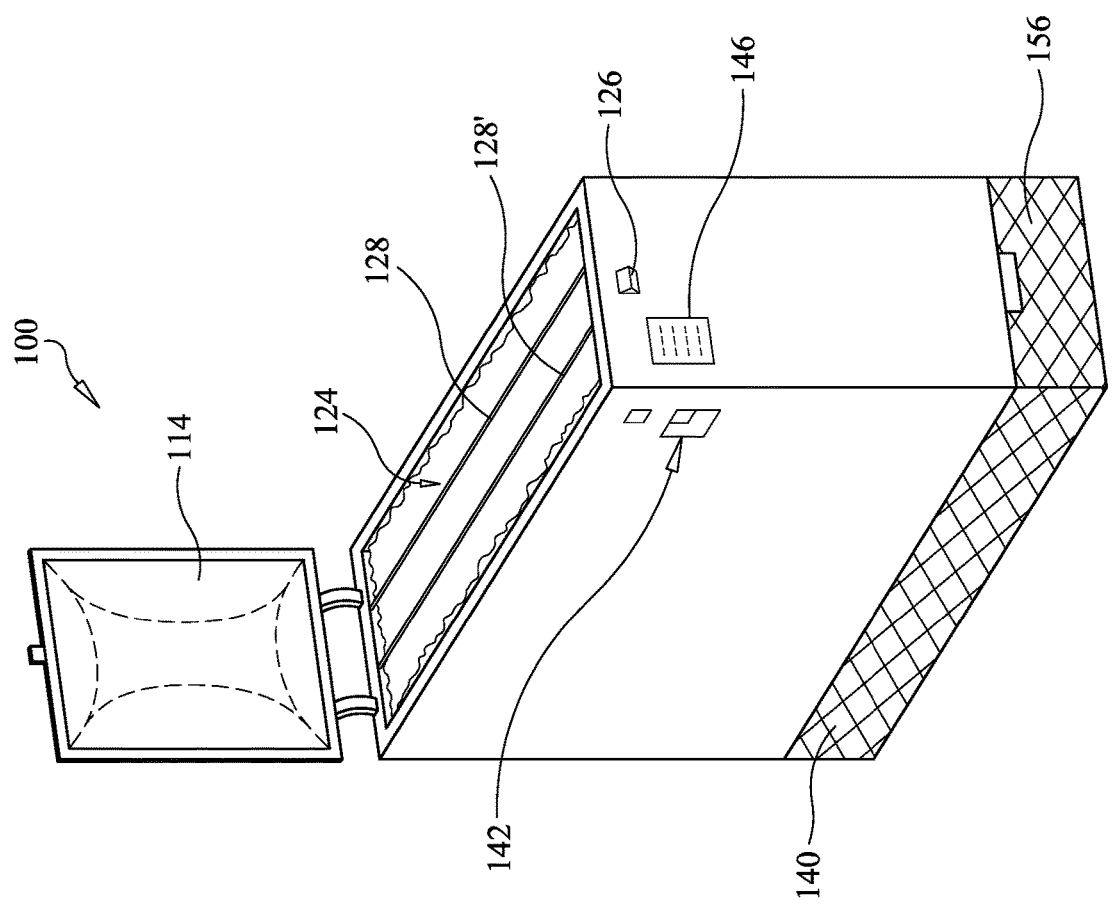
FIG. 1C shows another embodiment of the apparatus in accordance with one embodiment.

FIGS. 1A-IC show an exemplary apparatus 100 according to one or more embodiments of the present invention. Apparatus 100 comprises an outer casing 102 comprising of at least two or more rigid walls 104A, 104B, at least one outer perimeter wall 104A and a bottom wall 104B, wherein the outer perimeter wall 104A extends upward and substantially around the outer perimeter 106 of the outer casing 102, abutting and cooperating together with the bottom wall 104B that is disposed perpendicularly to the outer perimeter wall 104A, connecting together defining an inner cavity 108 adapted to form an inner receptacle area 110 configured for passage of the test tube, vial and/or pharmaceutical(s) being transported. In the exemplary embodiment shown in FIG. 1, apparatus 100 is rectangular in shape with five outer perimeter walls 104A and one bottom wall 104B. However, apparatus 100 may be constructed in any one or more of the following: different colors, shapes (e.g. rectangular, square, cylindrical, or any other geometric shape that may be used to practice the invention), and sizes (e.g. small, medium, large, extra-large, etc.) accommodating the quantity and/or size of the pharmaceutical(s) being transported. Apparatus' outer casing 102 is waterproof, constructed from firm, rigid material(s) ensuring that the apparatus is reusable, durable, waterproof, stain and/or rust resistant, e.g. high-density polyethylene or any other plastics, or metals such as steel or aluminum, and/or any other suitable materials generally known and used by persons skilled in the art.

Apparatus' inner cavity 108 is disposed within the outer casing's interior perimeter 112 and includes a liner 114 formed from a flexible impermeable material, substantially engaging the inner cavity 108, lining the inner walls 104C, 104D of the inner cavity 108 and abutting the container's top 116, separating the inner receptacle area 110 from the outer casing 102. Liner 114 may be formed from plastic, rubber and/or other similar flexible impermeable materials as are well known and used in the arts. In some embodiments, liner 114 may be formed from a composite of the impermeable material forming an interior lining coupled with a facing, comprising of fabric (e.g. velvet), burlap, neoprene, tarp, and/or other durable materials, with the fabric facing being visible from the inner receptacle area 110 for a more aesthetically pleasing look.

Apparatus 100 includes a flexible forming gel 118 encapsulated within, i.e. disposed between, the inner cavity 108 and the liner 114, wherein the forming gel 118 morphs and conforms to a shape of any content placed within the inner receptacle area 110 enveloping and holding such content secure and firmly in place. Forming gel 118 comprises a chemical solution that has sufficient viscosity, such that it is flexible enough to adapt and conform to the shape of the pharmaceutical's container placed within the apparatus 100, yet sufficiently firm to securely hold, e.g. an upright test tube being transported, while maintaining its cooling properties and sustaining its cool temperature for extended periods of time. In some embodiments forming gel 118 is a thermo-regulatory gel including for example, propylene glycol and/or some derivative and/or where the propylene glycol is a component of another chemical compound.

Apparatus 100 also includes an openable lid 120 hingedly attached to the container's top 116 and the inner receptacle area 110 via hinges 122, 122' to a main storage compartment 124, closeable by one or more closing means 126, 126' e.g. latches 126, 126' that fasten and secure the lid 120 and/or provide access to the inner receptacle area 110. Alternatively, other suitable forms of closing means 126, 126' such as locks, self-closing hinges, hooks, loops, snap fasteners, buttons, hook and loop fastener (i.e. VELCRO) or zippers may be employed to close the lid 120.

The lid 120 is configured to transition the apparatus's outer casing 102 between an open position and a closed position. In some embodiments, the lid 120 is completely removable, while in other embodiments, the lid 120 may be hinged and calibrated such that it provides maximum opening without being completely removable. However, it will be appreciated by those skilled in the arts of the invention that any form of a lid 120 may be employed without departing from the scope of the invention. Lid 120 may be constructed from the same material as the outer casing 102 and may include insulation and/or similarly outfitted with a liner 114, including the forming gel 118 disposed between the lid's outer casing 102 and the lid's interior perimeter 112' providing overhead support from the lid 120 for the container's contents, and keeping the upper portions of the apparatus 100 cool when closed. In some embodiments, lid 120 may be constructed from some other type of waterproof, firm and sturdy material that differs from the outer casing 102.

In some embodiments, apparatus' main storage compartment 124 includes at least one or more removable dividers 128, 128', removably affixed to the inner walls 104C, 104D of the inner receptacle area 110 dividing the main storage compartment 124 into sub-compartments 130, 130', 130" accommodating a plurality of test tubes and/or vials and/or pharmaceutical supplies 102 of different shapes and sizes. The removable dividers 128, 128' may be constructed from paper, cardboard, wood, plastic and/or any other materials that are well known and used in the arts for dividing/separating receptacle areas. In some embodiments, removable dividers 128, 128' may be slotted into grooves 132, 132' that may be scored along the sides of the interior perimeter 112 of the main storage compartment 124 securely holding the removable dividers 128, 128' in place. Each sub-compartment 130, 130', 130" of the inner receptacle area 110 forms its own discrete receptacle area to retain and house the pharmaceutical(s) being transported. The forming gel 118, substantially disposed within the liner 114 of the interior perimeter 112 provides vertical, lateral and/or base support for the content being transported. In some embodiments the inner receptacle area 110 includes shelves 134, 134' providing horizontal support that further compartmentalize the sub-compartments 130, 130', into additional surfaces, storage and stability for the pharmaceutical during transport.

Apparatus 100 comprises an activation switch 136 enabled for powering the apparatus' programmable monitoring unit 138 "ON" or "OFF" a shown in FIG. 2, when it is operably connected to its power source 140, i.e. at least one rechargeable battery 140, an AC charger for electrical power that charges/recharges the rechargeable battery 140, and/or via a charger port for portable charging of rechargeable batteries. Once the apparatus 100 is powered ON, the monitoring unit 138, which is mounted on the outer casing 102 is programmable and may be used to control the apparatus' internal temperature settings for transport via a thermostat 142 and aid in the monitoring of the battery 140, temperature fluctuations, logistics tracking, collecting and reporting various metrics and the like, such that the monitoring unit's digital display screen 144 will for example, display battery indicators, warnings, alarms, notifications, and the like.

In some embodiments, the monitoring unit 138 may be used to regulate the internal temperature of the apparatus 100 by controlling the apparatus' refrigerating element's fan and/or compressor motor to remove hot air from the apparatus' condenser and force cool air over the evaporator to create the desired cool temperature within apparatus 100. Monitoring unit's programmable display screen 146 with keypad may also be used to input/display information concerning the patient, e.g. including but not limited to: name, age, social security and/or identification number, physician, blood type, and the like. Additional information may be programmable and/or displayed on the display screen 146, such as but not limited to: date, scheduled delivery date and time, delivery destination, remaining time for viability, pharmaceutical name, hospital, and the like.

Users of the monitoring unit 138 may be authenticated by any one or more of the following authentication means 148: password verification (via the monitoring unit's keypad), keys, and/or biometric verification means. Biometric verification means 148 may comprises of hardware aspects for authenticating the identity of the user and may be disposed in communication with a computer processor and a biometric scanner, for example, a fingerprint scanner, facial scanner, hand geometry scanner, a palm geometry scanner, iris scanner, retina scanner, and/or a user interface, which may include an audio receiving circuit capable of receiving audio signals at predetermined frequencies and/or with additional hardware complete with electronic circuitry and such other biometric verification means that are known and used in the arts, wherein the computer processor controls the functionality of the biometric scanner, generating the varied algorithms for storage of initial valid biometric samples, stored as biometric identifiers for subsequent validation of biometric samples.

In some embodiments, authentication means 148 may comprise of software aspects while in other embodiments, authentication means 148 comprise of both hardware and software aspects. In some embodiments, the authentication means 148 may be stored on a computer readable storage medium in the monitoring unit 138.

In another aspect of an embodiment of the present invention, monitoring unit 138 may also include a processing module 150 that controls and/or coordinates all operations of the monitoring unit 138, making all determinations for the monitoring unit 138, including those functions which are not performed or covered by the other monitoring unit modules. Processing module 150 may comprise of hardware, e.g. a processor, and also include software aspects, e.g. computer program product having computer executable instructions necessary for the execution/implementation of all operations disclosed in aspect(s) of embodiment(s) of the present invention.

Apparatus 100 also includes a base 152, comprising of a housing 154 shaped to substantially enclose the bottom of the apparatus 100 within the housing's primary aperture, i.e.

a cradle, where the housing 154 is adapted to be releasably locked together with the main storage compartment 124 in a connected position forming a unitary device with the apparatus 100 such that the apparatus 100 would not otherwise require a bottom panel cover for the apparatus' internal battery(ies) 140 positioned within. In some embodiments, the base's housing 154 may be configured with an access panel 156 enabling access to the rechargeable batteries 140, 140', e.g. rechargeable titanium batteries that may have a battery life of six (6) hours or more. In some embodiments, the apparatus 100 comprises an AC charger for electrical power that charges/recharges the rechargeable batteries 140, 140'.

The rechargeable batteries 140, 140' supply primary power to the apparatus' compact refrigerating element 158 that includes hardware and/or refrigerant material disposed within the base 152, wherein the refrigerating element 158 is capable of maintaining temperature within a prescribed temperature range for extended periods of time upon being activated by the activation switch 136. In some embodiments, the apparatus' refrigerating element 158 may need to be precooled prior to any transportation of the pharmaceutical. In some embodiments, power may be supplied by solar cells, or an external charger port. Nonetheless, battery 140 is a part of the apparatus' power circuitry module to supply either primary or supplemental power for powering the refrigerating element's microprocessor, which cools the apparatus 100 and powers the monitoring unit 138 in order to perform the various functions listed herein. In some embodiments, apparatus 100 includes a port 160, e.g., a mini-USB port 160, operably engaged for transferring data to a remote monitoring center and/or a handheld monitoring unit, e.g. measured parameters, tracked metrics, and/or to attach an external power supply to charge the battery 140, which is part of the electronic circuitry. Battery 140 may be positioned internally within the base 152, on the exterior, or accessible from the exterior surface of the apparatus 100.

In some embodiments, apparatus 100 includes insulation 162 that insulates the internal storage compartments 130, 130', 130" aiding in protecting the transported content from exterior climate conditions and/or adverse elements (e.g. water) thereby assisting in maintaining the desired cool temperature. Exemplary insulation materials may include a substantially rigid insulating material having a relatively low thermal conductivity and being relatively light weight, for example NEOPRENE, POLYSTYRENE (STYRENE), POLYETHYLENE, VIP (Vacuum Insulation Panel), ABS and COROPLAST®, and/or TEMPSHIELD®. In some embodiments, insulation 162 is visibly located on the interior of the storage compartment and substantially surrounds each receptacle area 164, 164', 164" of the sub-compartments 130, 130', 130", while in some embodiments, the insulation 134 is hidden within the interior walls of the inner storage compartments 130, 130', 130" and the apparatus' outer casing 102. In one embodiment, the lid's interior 136 comprises of foam insulation preventing water from encroaching into the apparatus 100, i.e. the insulation is an effective water barrier to protect the transported blood and/or pharmaceutical and the like, as well as it prevents the transmittal of external heat from compromising the apparatus' 100 contents.

In some embodiments, apparatus 100 comprises a pouch 166 as shown in FIG. 3, which may be insulated and includes lifting/carrying means 168 that includes but is not limited to any one or more of the following: adjustable shoulder strap(s), handle(s), handgrip and any other carrying means 168 that are well known and used in the arts.

Depending on the carrying means 168, the apparatus 100 may be conveniently lifted and/or carried by the shoulder strap or lifted using one or more handles or grip. Pouch 166 may be constructed from a strong, but flexible material, e.g. fabric (e.g. cotton, burlap), neoprene, tarp, leather, plastic, rubber, and/or other durable materials that are known and used in the arts. Pouch 166 further comprises at least two or more walls 104A', 104B', a perimeter wall 104A' and a bottom wall 104B', wherein the at least one perimeter wall 104A' extends upward and around, abutting and cooperating together with the bottom wall 104B' that is disposed perpendicularly to the perimeter wall 104A', connecting and defining an open receptacle area 110' that accesses the pouch's interior and is configured for passage of the medical transport container 100. Pouch 166 comprises of a viewing window 170, which may be defined by an aperture within the perimeter wall 104A', and in some embodiments a transparent film is adhered to, and covers the aperture, defining the viewing window 170 through which the monitoring unit 138 and its digital display screen 146 can be viewed and accessed.

Monitoring unit 138 further comprises communication means 172 operably engaged to a sensor that senses the apparatus' internal temperature, registers the readings that are either stored in the monitoring unit 138 or transmitted via the communication means 172 to a remote monitoring center. Communication means 172 may comprise of a wireless transmitter or a transceiver that transmits and/or receives signals for communications via Wi-Fi, SMS text via a cell phone, internet, or local area network to a remote monitoring center to retrieve the tracked metrics regarding for example, any temperature fluctuations and/or warnings. In this manner, if for example, the temperature has spiked, the refrigerating element 158, or the power source lost power generating an alarm event, an alarm can be triggered for sounding or displaying an alarm condition on the displaying screen 146, and/or the tracked and transmitted metrics for the alarm event can be either detected/communicated remotely.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements and compositions described herein or in the features or in the sequence of features of the methods described herein without departing from the spirit and scope of the invention as described in the following claims.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. Modifications and substitutions by one of ordinary skill in the art are considered to be within the scope of the present disclosure.

What is claimed is:

1. An apparatus for transporting pharmaceuticals comprising:
    an outer casing comprising at least two rigid walls made up of an outer perimeter wall and a bottom wall, wherein the outer perimeter wall extends upward and substantially around an outer perimeter of the outer casing, abutting and cooperating with the bottom wall that is disposed perpendicularly to the outer perimeter wall, together forming an inner cavity adapted to form an inner receptacle area:
    the inner cavity includes a liner formed from an impermeable material, substantially engaging the inner cavity, lining inner walls of the inner cavity and abutting a top of the apparatus and including a flexible forming gel disposed between the inner cavity and the liner, wherein the flexible forming gel morphs and conforms to a shape of a content within the inner receptacle area, holding the content secure and firmly in place;
    an openable lid is attached to the top of the apparatus and the inner receptacle area; and
    a refrigerator is included, and is capable of maintaining temperature within a prescribed temperature range for extended periods of time upon being activated;
    a base comprising of a housing shaped to substantially enclose a bottom of the apparatus within a primary aperture of the housing, where the housing is adapted to be releasably locked together with the main storage compartment in a connected position forming a unitary device with the apparatus;
    grooves scored along sides of an interior perimeter of a main storage compartment securely holding removable dividers in place;
    wherein at least one or more removable dividers removably affixed to the inner walls of the inner cavity;
    wherein the flexible forming gel provides any one of the following support for the content being transported: vertical, lateral and/or base support;
    wherein the lid is configured to transition the outer casing between an open position and a closed position;
    wherein the lid further comprises insulation and/or the liner, wherein the lid includes the flexible forming gel, providing overhead support from the lid for the container's contents;
    wherein a digital display screen is provided, and further comprises authentication means that may be any one or more of the following: password verification, keys, and/or biometric verification;
    wherein the biometric verification means comprise of a computer processor disposed in communication with a biometric scanner, and/or a user interface;
    wherein the biometric scanner comprises of any one or more of the following: a fingerprint scanner, facial scanner, hand geometry scanner, a palm geometry scanner, iris scanner, and/or retina scanner.

2. The apparatus of claim 1, wherein the outer casing may be constructed in any one of the following shapes: rectangular, square, cylindrical, or other geometric shape.

3. The apparatus of claim 1, further comprising a power source that may include any one or more of the following: a rechargeable battery, an AC charger, and/or a charger port.

4. The apparatus of claim 1, further comprising a communication member that includes a wireless transmitter or a transceiver.

5. The apparatus of claim 1, further comprising a pouch that comprises of at least two or more walls cooperating together, connecting and defining an open receptacle area that accommodates the apparatus.

6. The apparatus of claim 5, the pouch further comprising insulation.

7. The apparatus of claim 5, the pouch further comprising carrying means that includes but is not limited to any one or more of the following: adjustable shoulder strap, handle, or handgrip.

8. The apparatus of claim 5, the pouch further comprising a viewing window defined by an aperture within the pouch's perimeter wall.

9. The apparatus of claim 1, further comprising a transparent film adhered to, and covering the primary aperture thereby defining the viewing window.

* * * * *